United States Patent
Yang et al.

(10) Patent No.: US 7,469,696 B2
(45) Date of Patent: Dec. 30, 2008

(54) THERMAL DROP GENERATOR

(75) Inventors: Xiaofeng Yang, Corvallis, OR (US); Rod Alloy, Corvallis, OR (US); Kenneth E. Truba, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 729 days.

(21) Appl. No.: 11/044,660

(22) Filed: Jan. 27, 2005

(65) Prior Publication Data
US 2006/0077217 A1   Apr. 13, 2006

(51) Int. Cl.
*A61M 11/00* (2006.01)
(52) U.S. Cl. .............................. 128/200.14; 128/200.16
(58) Field of Classification Search ............ 128/200.14, 128/200.16; 347/15; 239/102.2, 690
See application file for complete search history.

(56) References Cited

U.S. PATENT DOCUMENTS

| | | | |
|---|---|---|---|
| 5,881,716 A | 3/1999 | Wirch | |
| 6,543,879 B1 * | 4/2003 | Feinn et al. | 347/40 |
| 6,547,351 B1 * | 4/2003 | Wilson | 347/9 |
| 6,595,611 B1 * | 7/2003 | Ruffino | 347/5 |
| 2002/0073990 A1 | 6/2002 | Noolandi | |
| 2002/0092519 A1 * | 7/2002 | Davis | 128/200.14 |
| 2003/0081072 A1 | 5/2003 | Trueba | |
| 2003/0186474 A1 | 10/2003 | Haluzak | |
| 2004/0039355 A1 | 2/2004 | Gonzalez | |

* cited by examiner

*Primary Examiner*—Steven O Douglas (57) ABSTRACT

A silicon die having an orifice layer with plural openings formed therein defines a drop ejection device for use in a handheld inhaler. An underlying control layer defines fluid chambers, each carrying a heat transducer. A control system energizes selected heat transducers to heat fluid in the chambers, vaporizing the fluid, which is ejected through the orifices in small droplets.

27 Claims, 6 Drawing Sheets

FIG. 14 ably eject drops without problems such as gulping in bubbles.

THERMAL DROP GENERATOR

TECHNICAL FIELD

This invention relates to a thermal drop generator apparatus capable of generation of aerosolized droplets of liquid.

BACKGROUND OF THE INVENTION

Medications are often delivered to patients in the form of inhaled aerosols—gaseous suspensions of very fine liquid or solid particles in which medications are entrained. So-called pulmonary delivery of medication is in many instances a very efficient manner of delivering biological and chemical substances to the patient's bloodstream. Pulmonary delivery is especially efficient when the medication is delivered with a digitally controlled device such as a "metered dose inhaler" ("MDI") or other type of inhaler that incorporates ejector heads that are suitable for creating aerosols having very small droplet size. Such inhalers are often used to deliver asthma medications directly into a patient's lungs where the medications have a rapid anti-inflammatory effect. MDIs may also be used for systemic delivery of medication where the aerosolized droplets of medication are delivered deep into the lung tissue where the medication is rapidly absorbed into the patient's blood stream.

The most effective pulmonary drug delivery is accomplished when the medication is delivered in very small, aerosolized droplet directly to the alveoli—the tiny air sacs in the innermost lung tissue known as the alveolar epithelium—because the medication is transferred into the patient's bloodstream very rapidly. Delivery of medication to the alveoli is most efficiently accomplished when the medication is delivered in very small drops entrained in an aerosol. Thermal-type drop generators may be used to generate aerosolized medications having small drop sizes. However, there is an ongoing need for a droplet generator that can reliably produce very small-volume droplets with a generally uniform size distribution for entrainment in aerosols.

BRIEF DESCRIPTION OF THE DRAWINGS

Apparatus and methods for carrying out the invention are described in detail below. Other advantages and features of the present invention will become clear upon review of the following portions of this specification and the drawings.

DETAILED DESCRIPTION OF ILLUSTRATED EMBODIMENTS

The device of the present invention is medicament aerosol generator or an inhalation system including a drop ejection device that receives fluid from a fluid supply system. The drop ejection device is coupled to a controller and includes a plurality or multiplicity of individual drop generators, each of which ejects droplets of aerosolized fluid under the influence of the controller.

The inhalation system of the present invention includes circuitry that is electrically coupled to the drop generators and is configured to provide drop ejection pulses to each of the drop generators. By way of illustrative embodiment, drop ejection pulses are current or voltage pulses that are delivered to each of the drop generators. That they are delivered to each of the drop generators is to be understood to mean that they can be delivered to drop generators that are separately addressable or drop generators that are coupled in a parallel or serial arrangement wherein they are not individually addressable.

The inhalation system of the present invention also includes a fluid delivery system configured to deliver fluid to the drop generators at a controlled pressure level when measured adjacent the drop generators. Stated another way, the drop generators receive fluid having a controlled pressure level or range of pressure levels. As a result of the drop generator design and the characteristics of the fluid being delivered to the drop generators, the drop generators have a stable operating range that extends to gauge pressures below about −10 inches of water. Most preferably, the gauge pressure operating range is between about less than −10 inches of water to about −15 inches of water, but the drop generators have a stable operating range for gauge pressures anywhere in a range from below about −10 inches of water to about −45 inches of water.

As used herein, gauge pressure means the pressure difference between the pressure in question and outside atmospheric pressure. Gauge pressures for fluid drop generators are measured in inches of water (rather than mercury or PSI for example) because they tend to be of relatively low magnitude. References to a stable operating range, mean a range of pressures through which the drop generators can reli- By way of illustrative embodiment, the drop generators are thermal type drop generators wherein each drop generator includes a nozzle or orifice that is disposed proximate to a current or voltage pulse activated resistor with supplied fluid therebetween. In response to receiving a pulse, the resistor generates a drive bubble in the fluid that forces ejection of an aerosol particle or droplet from the nozzle. The present invention is not limited to thermal drive bubbles, however, and includes designs that may incorporate piezo-activated drop generators.

By way of illustrative embodiment, the ejection device of the present invention includes at least 1000 fluid drop generators and preferably more than 9000 fluid drop generators. The circuitry delivers drop ejection pulses (meaning current or voltage or charge pulses) to each of the drop generators at a rate of at least 25 KHz and preferably at a frequency of at least 200 KHz.

Pulmonary drug delivery is most effective if the drop size is precisely controlled. Several physical characteristics of the droplets are important in providing effective pulmonary delivery so that medication delivered in the aerosolized droplets is quickly transferred into the blood stream. These include extremely small drop diameters, preferably between about 0.1 to 15 μm with a standard deviation of about 20% of the target drop size. Other characteristics of the inhalation system are similarly important, including a turn-on-energy (TOE) of about 0.014 μJ or less, a drop velocity of about 10 m per second or more as the droplets are expelled from nozzles, and a nozzle firing frequency of at least about 25 KHz, and more preferably about 200 KHz.

The present invention comprises an ejector head architecture capable of meeting these design criteria and additional criteria as detailed herein.

By way of background and to provide context, and with specific reference now to FIGS. 1, 2 and 3, the illustrated embodiment of the drop ejection device will be described as it is embodied in pharmaceutical delivery apparatus 10, which in this case is a handheld pulmonary delivery mechanism known as a metered dose inhaler (MDI) and is at times referred to herein as MDI 10. MDIs such as the MDI 10 described herein are used for the delivery of aerosolized medications such as asthma medication and there are many variations of MDI delivery systems on the market. An MDI typically combines a drug with a propellant in a container that may be pressurized. The drug may be in the form of a liquid or a fine powder. Actuation of the device releases metered doses of aerosolized drug that is inhaled by the patient.

Figure 1:
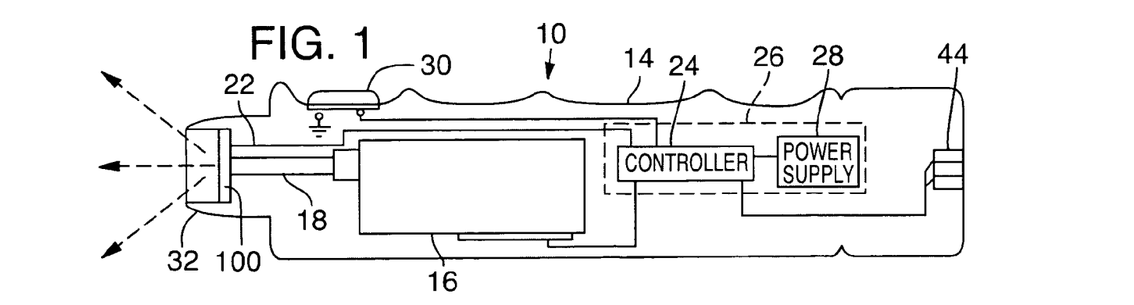
FIG. 1 is a schematic side elevation view of a metered dose inhaler apparatus, which is one example of a medication delivery apparatus in which the illustrated embodiment of drop generator of the present invention is incorporated.
Figure 2:
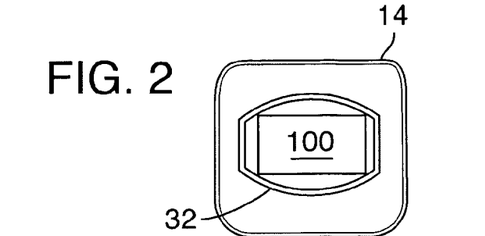
FIG. 2 is left side elevation view of the metered dose inhaler shown in FIG. 1, illustrating the front or mouthpiece end of the inhaler and the drop generator.
Figure 3:
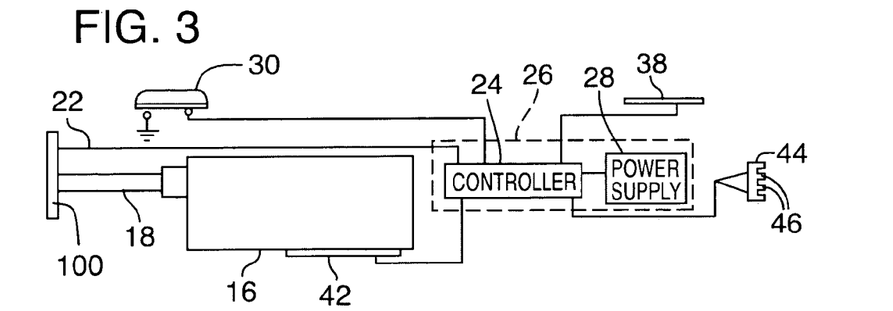
FIG. 3 is a schematic representation of an exemplary electrical circuit of the metered dose inhaler illustrated in FIG. 1.

It will be appreciated that the MDI 10 illustrated in FIGS. 1, 2 and 3 is intended only to illustrate one of many possible pharmaceutical containers and delivery systems that may incorporate the a thermal-type drop generator as described herein. As used herein, the term "medication" is used generally to refer to any fluid or compound, whether biological, chemical or other, delivered to a patient, whether for treatment of a medical condition or some other purpose. Other common words may be used interchangeably, such as "pharmaceutical," or "medicament" or "bioactive agent" and similar words.

Before turning to a detailed description of the drop generator, the primary components of container 10 will be described with specific reference to FIGS. 1, 2 and 3.

Container 10 comprises an inhaler housing 14 that is configured to contain a reservoir or supply 16 of medication, which as noted is typically provided in liquid form, often as a solution. The medication supply 16 is coupled, as for example by a needle and septum interconnection or other airflow regulator such as a thermal resistive element or piezo element, to a conduit 18 in the housing 14 so that the medication in supply 16 is directed to a drop ejection device, illustrated schematically at 100 and described in detail below, that carries multiple drop generators and which is configured for generating appropriately sized aerosolized drops of the liquid from the medication supply 16. It will be appreciated that the illustration of FIGS. 1 and 2 are schematic, and that an MDI must necessarily be designed to have the capability for the patient inhale a substantial volume of air with which the medication is mixed.

The drop ejection device 100 is electrically interconnected to a controller, shown schematically at 24, which is part of the MDI control system 26, for example with a flex circuit 22. Among other functions described below, controller 24 generates and sends suitably conditioned control signals to drop ejection device 100 to initiate firing of nozzles and thus delivery of the medication. The MDI control system 26 includes controller 24, a power supply 28 (such as batteries) and operator switch 30. The controller 24 is an integrated circuit, typically in a CMOS chip that responds to the switch signal by directing to the drop ejection device 100 controlled current pulses for firing the drop generators as required. It will be appreciated that the control system can be configured in any of a number of ways and, most preferably, integrated with the housing 14 of the inhaler. Controller 24 includes appropriate processors and memory components. In some circumstances the integrated circuitry that defines controller 24 may be incorporated into a real time clock circuit, and vise versa.

In the case where MDI 10 is configured for delivery of medication via inhalation by the patient, the drop ejection device 100 is located near a mouthpiece or nosepiece 32. The drop ejection device 100 illustrated in FIG. 1 is thus located inwardly of the mouthpiece 32 to allow the aerosolized medication to mix with airflow. It will be appreciated that the control system 26 and the arrangement and orientation of the drop ejection device 100 in housing 14 provide for both precise metering of the amount of droplets ejected and of the amount of medication expelled, as well as the generation of suitably small droplets. That is, the expulsion of the medication from the medication supply 16 need not be accompanied with other mechanisms for reducing the volume of ejected liquid to suitably small droplets. The ejection route of medication aerosolized out of mouthpiece 32 is shown schematically with a series of arrows in FIG. 1.

With reference to FIG. 3, a display panel 38 is used to alert the user of status information and other user-perceptible information. Display panel 38 may be any one of many kinds of displays such as a light emitting polymer sheet or LCD display.

MDI 10 may include a control sensor 42, which may be, for example, a temperature sensor operatively coupled to medication supply 16 so that the sensor is capable of detecting and monitoring the actual temperature of the medication contained within the supply reservoir 16. MDI 10 also preferably includes sensors such as appropriate circuitry in the drop ejection device 100 to monitor the pressure or the gauge pressure of fluid adjacent to the drop generators.

Suitable sensors 42 include integrated circuit temperature sensors such as thermisters and resistors, thin film metals, metal oxide semiconductor temperature sensors, CMOS or MOS transistors, bipolar transistors, circuits defining a Wheatstone bridge, and others. Suitable pressure sensors include transducers such as a piezo-electric device that generates a voltage in response to a pressure. Depending upon the specific usage, more than one sensor 42 and sensors of different types may be utilized.

Control system 26 includes a programming interface 44 connected to controller 24 and externally exposed at the rearward end of housing 14 (FIG. 1) for connection to an external computer. Programming interface 44 is a conventional interface that includes conductor pads 46 that interconnect the interface through traces (as in a flex circuit) and conventional buss interfaces to controller 24. The illustrated embodiment of programming interface 44 may be replaced, for example, with any suitable programming interface, including an infrared compliant data link, or other similar programming interface.

Figure 4:
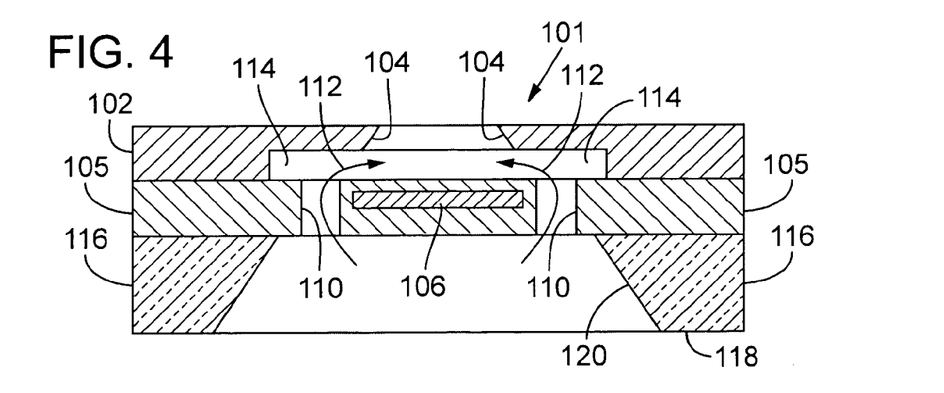
FIG. 4 is a schematic, enlarged cross sectional diagram illustrating a single nozzle structure in a drop generator made in accordance with an illustrated embodiment of the present invention.

Having described an illustrated embodiment of an MDI 10 in which a drop ejection device 100 according to the present invention may be used, reference is now made to FIG. 4, which illustrates in cross sectional schematic form a single drop generator 101 of the type that may be used in a drop ejection device 100 formed in accordance with one aspect of the present invention. Drop generator 101 is shown in cross section. Only one drop generator is shown in isolation in FIG. 4. But as will become clear, the drop ejection device 100 comprises multiple thousands of drop generators in order to generate sufficient droplets in a given application.

The drop ejector device described herein may be fabricated according to the disclosures in U.S. patent application Ser. Nos. 09/761,287 (Publication No. US 2002/0092519 A1) and 10/000,425 (Publication No. 2003/0081072 A1).

With continued reference to FIG. 4 an orifice layer 102 is constructed as a generally planar member having a nozzle or orifice 104 defined in it. The orifice layer 102 is overlies a solid control layer 105 that includes resistive heat transducer elements 106 (also referred to herein as resisters), one of which is shown in FIG. 4. Heat transducer elements 106 may further include circuitry and/or sensor capabilities to monitor gauge pressure at drop generators 101. Two inlets 110 are defined in the control layer 105 to allow the liquid to flow (as depicted by arrows 112) into a chamber 114, which defines a small reservoir for holding liquid prior to ejection of the liquid from the chamber through the orifice 104. The control layer 105 overlies a solid substrate member 116 that has one side 118 in communication with fluid from, for example, supply 16, and which defines an inlet chamber 120 through which fluid flows into inlets 110. For reference purposes, the internal height dimension of chamber 114 is about 2 μm, and the thickness of control layer 105 at nozzle 104 is likewise about 2 μm.

It will be appreciated that the word drop generator is used herein to describe generally the structures such as those shown in FIG. 4 for ejecting droplets, and, therefore, the word drop generator includes structures such as a nozzle or an orifice and a resister, and associated components.

The mechanism for ejecting the liquid from the chamber 114 is by energizing heat transducer 106 to generate in the liquid-filled chamber a vapor bubble, the expansion of which ejects the liquid through the orifice 104. For computational purposes the heat transducer 106 is considered a planar member (such as a thin-film resistor) that, upon actuation heats the liquid in the chamber to very rapidly vaporize the liquid and thus eject it through the orifice in the form of a small droplet.

FIGS. 5 through 8 illustrate several nozzle architectures that are of the type suitable for use in fabricating a drop ejector device.

Figure 5:
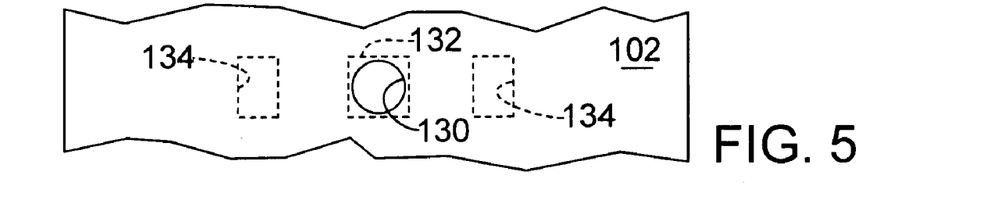
FIG. 5 is a top plan view of a single dual-inlet nozzle drop generator for use in a drop ejector device in an inhaler of the type shown in FIG. 1.

FIG. 5 illustrates in a top plan view the arrangement of the orifice layer 102 having an orifice 130, heat transducer 132 that underlies the orifice 130, and inlets 134 disposed on either side of the orifice. Liquid flows from chamber 110 (FIG. 4) into inlets 134 and chamber 114, and is vaporized and ejected through orifice 130 by energizing heat transducer 132.

Figure 6:
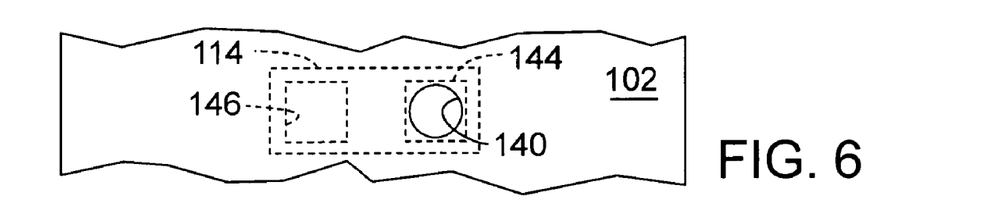
FIG. 6 is a top plan view of a single single-inlet nozzle drop generator for use in a drop ejector device in an inhaler of the type shown in FIG. 1.

FIG. 6 shows in a top plan view similar to the view of FIG. 5 an alternative arrangement where a single orifice 140 is formed in orifice layer 102. A heat transducer 144 is positioned in control layer 106 as detailed above below orifice 140. Fluid flows into chamber 114 through a single inlet 146.

Figure 7:
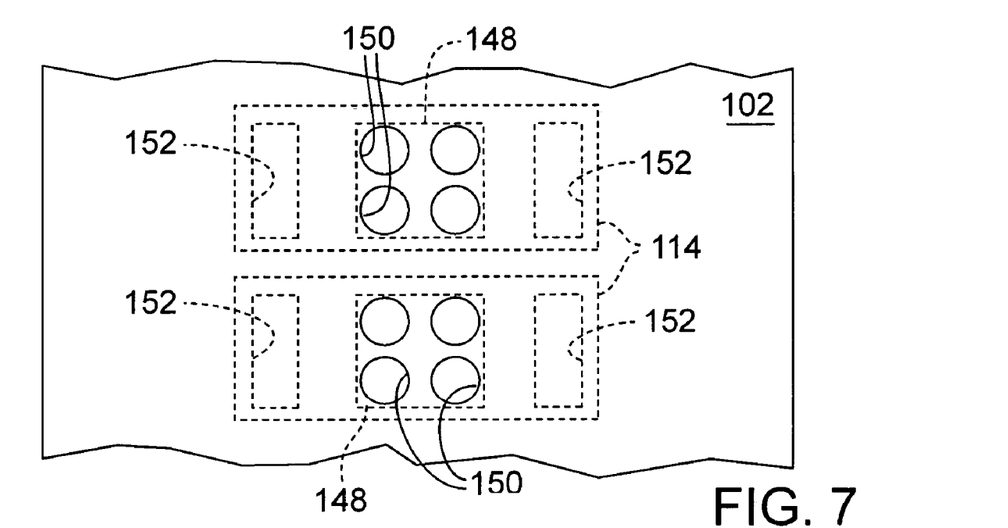
FIG. 7 is a top plan view of two dual-inlet, four nozzle drop generators for use in a drop ejector device in an inhaler of the type shown in FIG. 1.

FIG. 7 shows in a top plan diagram yet another alternative arrangement of orifice, resistor, and inlet components of an exemplary pair of chambers 114 as formed in accordance with the present invention. In the embodiment illustrated in FIG. 7, a relatively large resistor 148 is used and the orifice layer 102 is formed with four orifices 150 overlying the four corner portions of the resistor. The liquid provided to the resistor 148 flows through a pair of inlets 152, one inlet on each side of the resistor 148.

Figure 8:
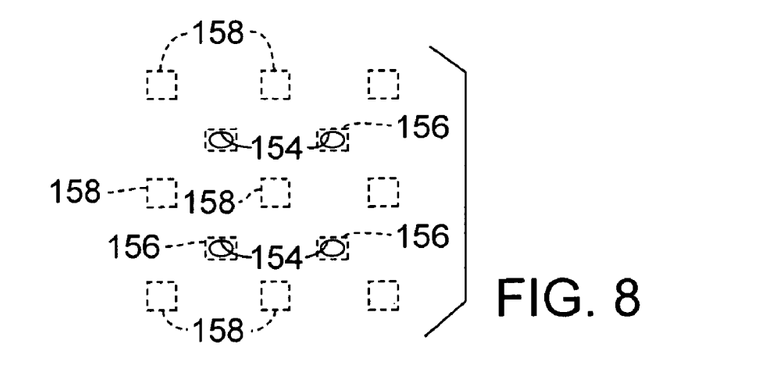
FIG. 8 is a top plan view of an array of nozzles drop generators exemplary of the type that may be used in a drop ejector device in an inhaler of the type shown in FIG. 1.

FIG. 8 is a schematic diagram illustrating yet another one of several ways of arranging a small group of nozzles on an orifice layer. The diagram of FIG. 8 is a plan view wherein the orifices 154 are above the resistors 156. The resistors 156 are connected by the control layer 106 to the control system 126. In this embodiment, the inlets 158 are square in cross section and arranged so that there are at least two inlets 158 adjacent to each resistor 156.

The spatial arrangement and relative positioning of the orifices and resistors shown in FIGS. 5 through 8 are for illustrative purposes only and other arrangements are contemplated. As one example, the orifices need not be aligned in a 90-degree grid as shown in FIG. 8. Rather, the resistors and orifices can be arranged in staggered columns and/or rows and the like.

In all instances described above, the hydraulic diameter of the orifices (e.g., 104, 130, 140, 150, 154) is preferably between about 2.0 μm and 3.0 μm, and more preferably about 2.6 μm. With this orifice size, the average droplet size expelled through each orifice is about 3 μm.

From the foregoing discussion it will be appreciated that the drop ejection device 100 comprises a semiconductor die that incorporates thousands of nozzles such as nozzle 101 from FIG. 4. The nozzles may be of the types illustrated in FIGS. 5 through 8, and the structure of drop ejection device 100 is detailed below.

Figure 9:
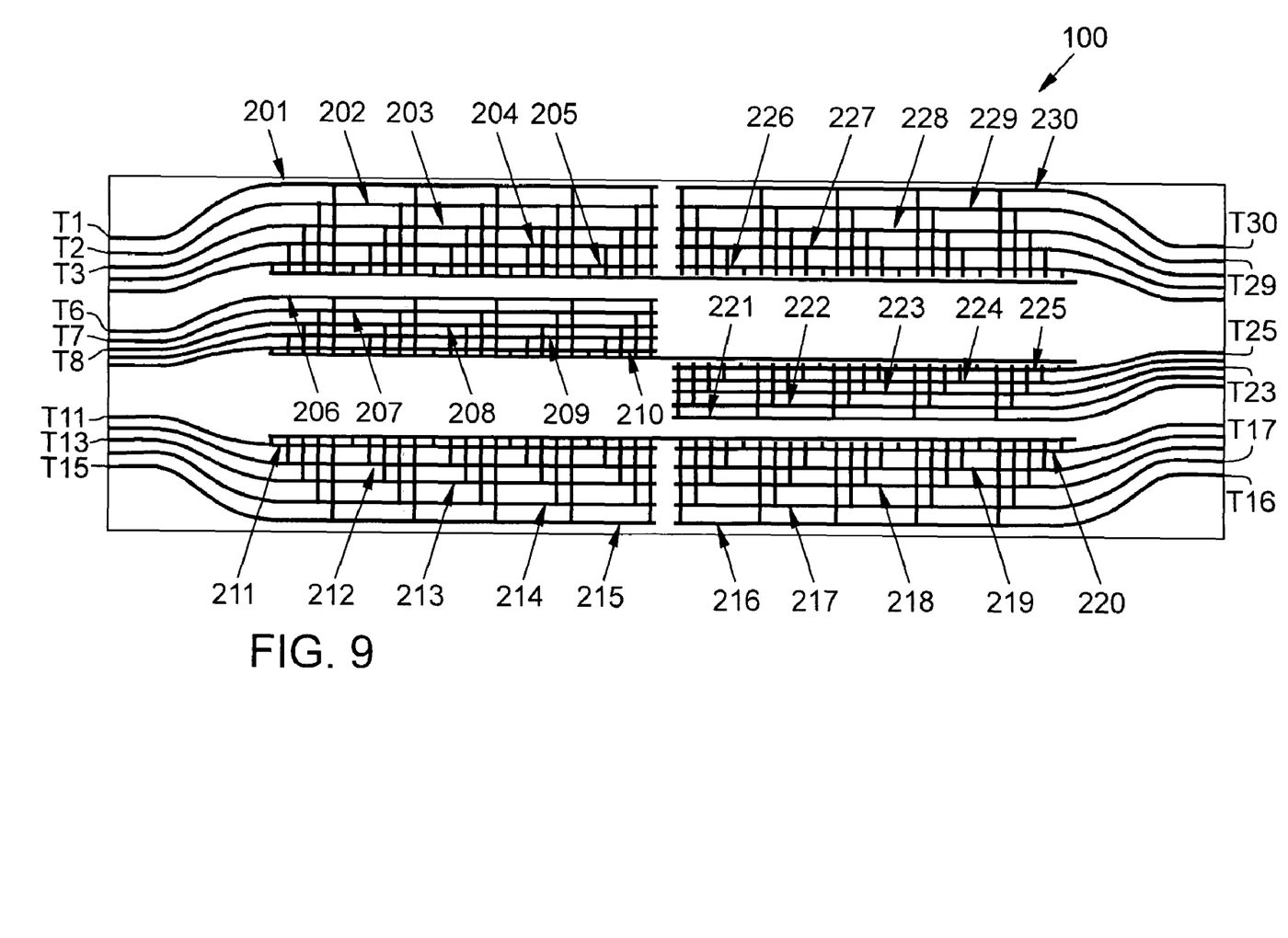
FIG. 9 is a schematic layout view of a die architecture illustrating one embodiment of a drop generator layout on a die.
Figure 10:
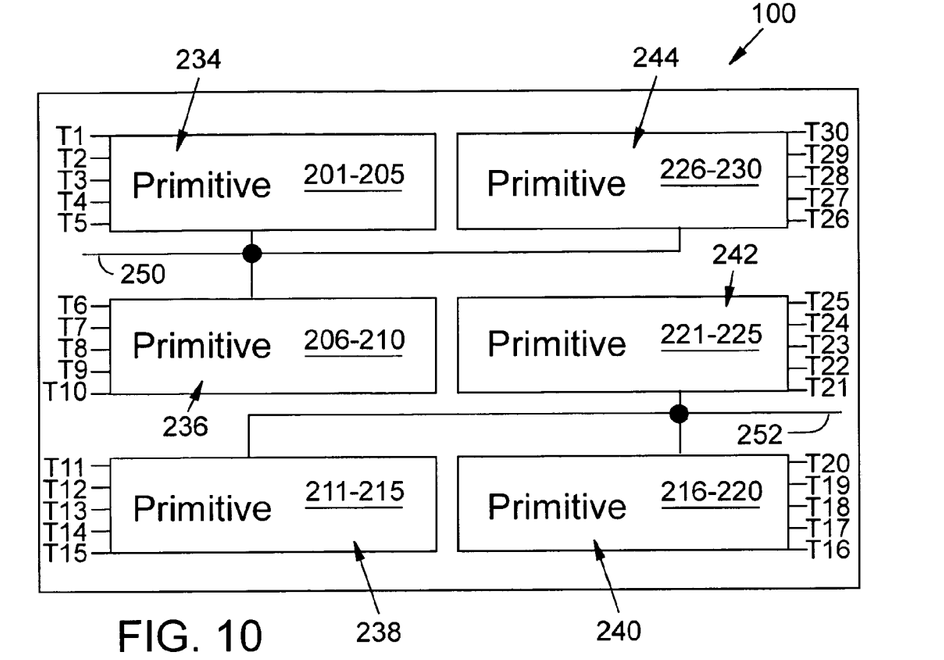
FIG. 10 is an enlarged schematic view illustrating the separate layout of nozzle firing groups on the silicon die schematically illustrated in FIG. 9.
Figure 11:
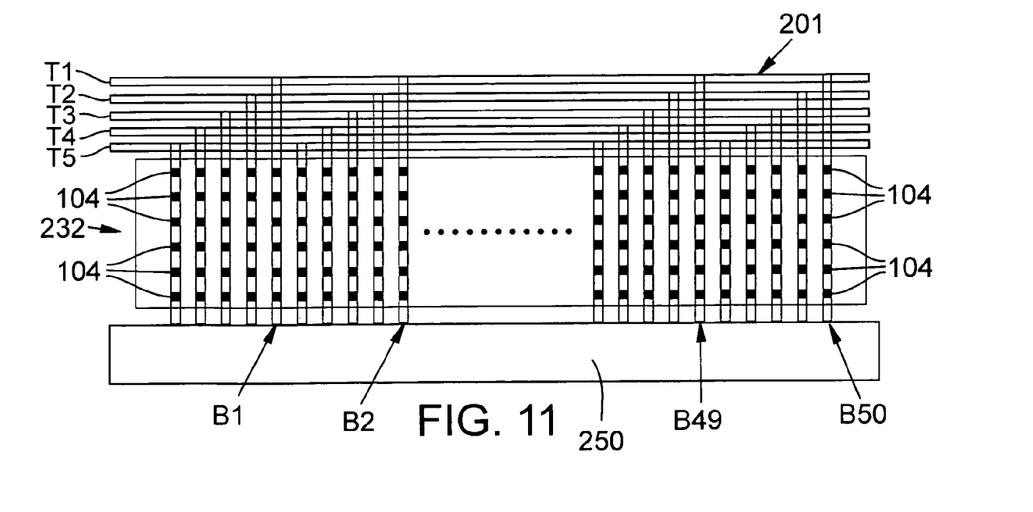
FIG. 11 is an enlarged schematic illustration of one primitive or nozzle firing group of the type shown in FIGS. 9 and 10.

Turning now to FIG. 9, an exemplary die schematic is shown in top plan view to illustrate the die layout architecture of drop ejection device 100. Drop ejection device 100 comprises 30 primitives (labeled with arrows 201, 202, 203, etc. through 230, which will be understood to be schematic representations of the primitives in which each reference number (e.g., 201, 202, etc.) identifies a group of nozzles electrically interconnected by an electrical trace, as detailed below). The primitives are also referred to herein as nozzle firing groups. Each nozzle firing group comprises 300 individual orifices such as orifice 104, FIG. 4. As detailed below, each of the 300 individual orifices in a nozzle firing group is controlled by control system 26 to fire simultaneously. For die layout purposes, the 30 nozzle firing groups are laid out in six layout blocks, as best illustrated in the schematic layout of FIG. 10 where the layout blocks are given reference numbers 234, 236, 238, 240, 242 and 244 respectively. FIG. 11 is a schematic close up detail of one nozzle firing group, in this case for reference purposes, nozzle firing group 201. With specific reference to FIG. 11, each nozzle firing group such as 201 is formed above the fluid delivery slots, such as fluid delivery slot shown schematically with reference number 232. The fluid delivery slot 232 is in communication each of the firing orifices in the firing group through chambers 120 described above with reference to FIG. 4. As noted, each firing group such as firing group 201 has 300 nozzles. Thus, each firing group or primitive has 50 branches (labeled in FIG. 11 with numbers B1, B2, etc. through B50) laid out in parallel arrangement. Each of the 50 branches has six individual orifices 104, represented in FIG. 11 with darkened squares. The six individual orifices 104 are laid out in series. As detailed above, each orifice 104 is associated with a heat transducer element 106. As noted above, each orifice 104, the associated heat transducers and chambers, comprise individual nozzles.

With returning reference to the nozzle firing group 201 in FIG. 11, each group has 50 branches (B1, B2, B3, . . . B50) in parallel and each branch has 6 orifices 104 (and associated resisters) arranged in series such that each group has a total of 300 orifices 104. Accordingly, drop ejection device 100 comprises 9000 individual nozzles, which may be arranged according to any of the configurations described above with respect to FIGS. 5 through 8. With this number of nozzles, drop ejection device 100 has a nozzle density of greater than about 100 nozzles/mm$^2$, and more preferably greater than about 250 nozzles/mm$^2$.

The control electronic interconnections of drop generator head 100 are shown schematically in FIGS. 9 through 14. The electrical architecture and electronics control under controller 24 are designed to minimize drop merging as drops are expelled simultaneously from different orifices, and to maximize the firing frequency and flux. MDI 10 is preferably a handheld device powered by a battery. As such, the control electronics must be configured to preserve and maximize optimal battery operational life. That is, the MDI 10 must be operable with low enough voltage and current that a battery, group of batteries, or a charge pump circuit can power the device. Moreover, parasitic power loss must also be minimized.

Each of the six layout block 234 through 244 comprises five nozzle firing groups, for example, 201 through 205 for layout block 234, 206 through 210 for layout block 236, and so on. Each of the five nozzle firing groups in a layout block has one independently controlled terminal, such as that defined by an electrical trace. In FIGS. 10 and 11 these traces are given reference numbers T1, T2, etc. through T30. The opposite ends of the traces from three layout block are electrically interconnected to define a COM terminal. Thus, the traces from the primitives in layout block 234 (e.g., 201-205), 236 (e.g., 206-210), and 244 (e.g., 226-230) are connected to COM 250. Likewise, the traces from the primitives in layout block 238 (e.g., 211-215), 240 (e.g., 216-220), and 242 (e.g., 221-225) are connected to a second COM 252. Each of the COM terminals COM 250 and COM 252 has electrical control over 15 primitives, and as noted there are 300 nozzles per primary. Therefore, each COM terminal has electrical control over 4500 nozzles.

Figure 12:
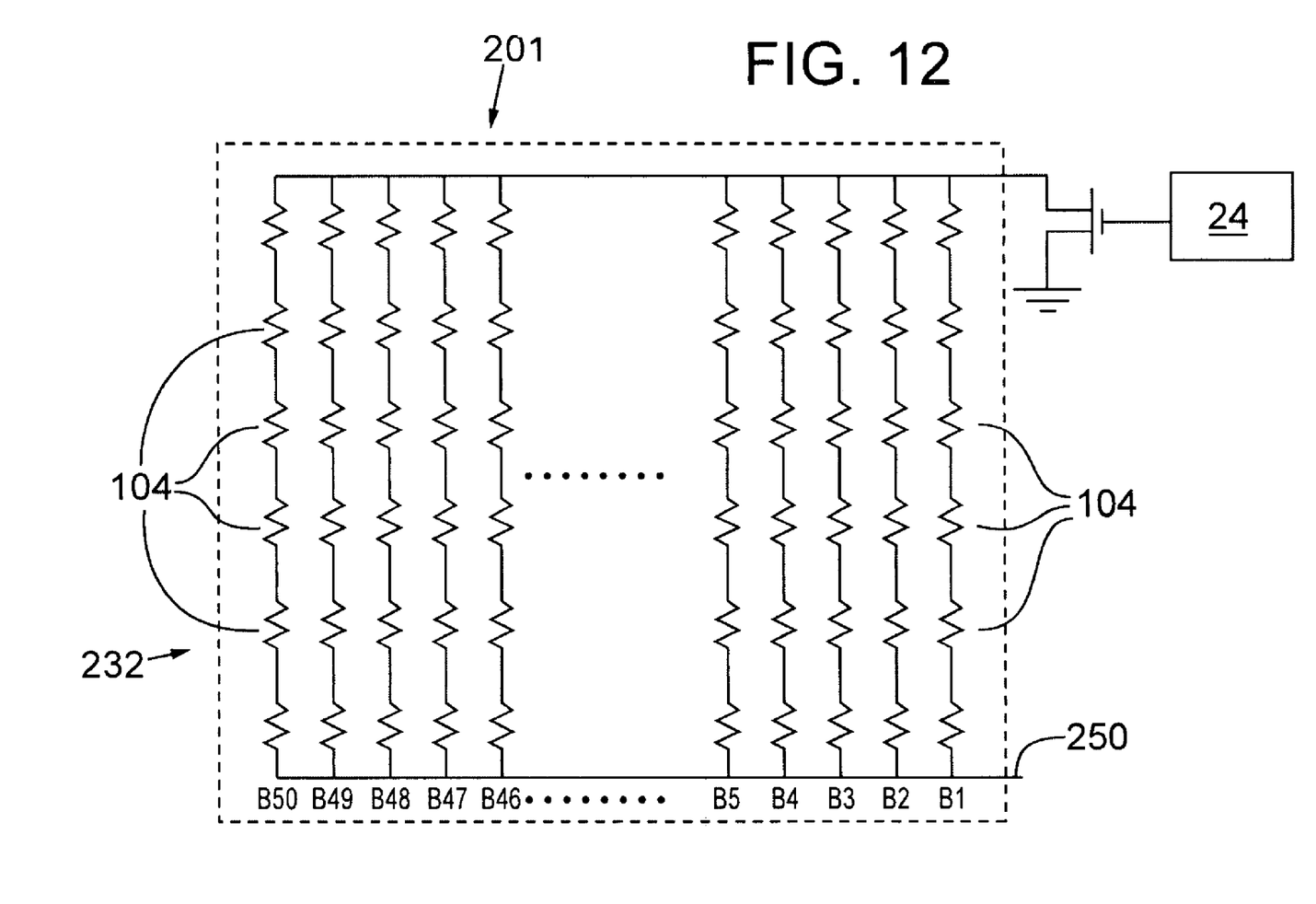
FIG. 12 is an enlarged schematic illustration of one primitive or nozzle firing group similar to that shown in FIG. 11 and showing the positions of the heat transducers and the electrical interconnections.
Figure 13:
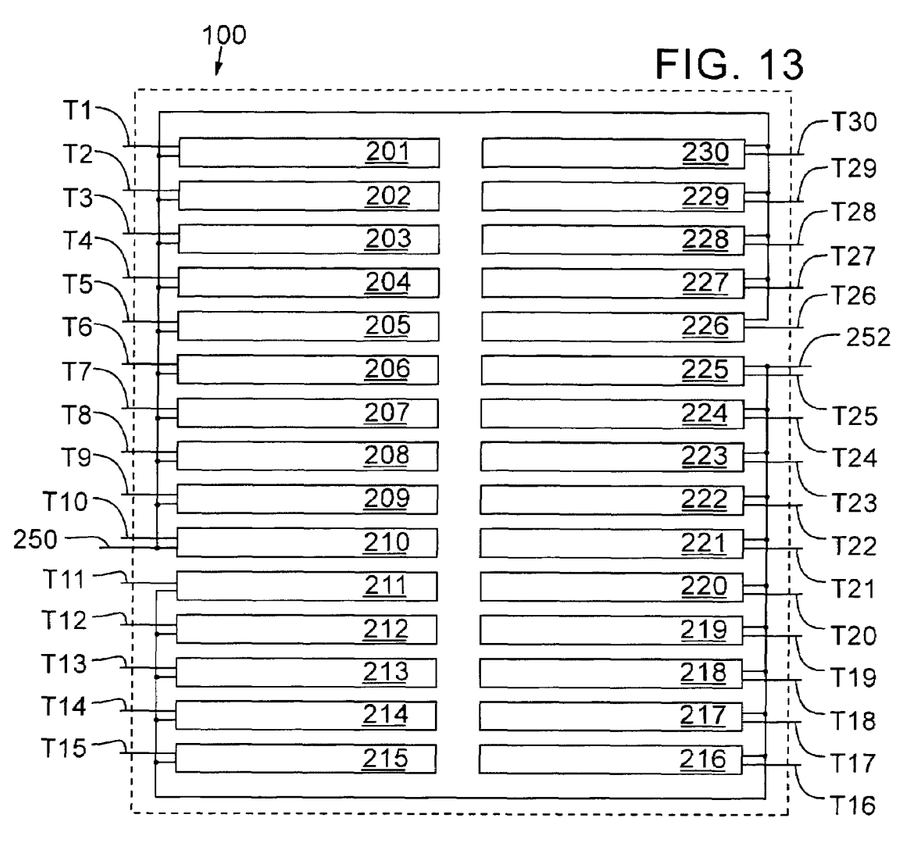
FIG. 13 is an illustrated electrical circuit schematic for the drop generator head.

Referring now to FIG. 13 it may be seen that drop ejection device 100 comprises 30 firing groups (primitives). As detailed below, the controller 24 preferably simultaneously energizes the primitives in pairs of two in a sequential order to thereby minimize the voltage drop on the traces, so that parasitic power loss and performance variation are minimized. FIG. 12 is a schematic electrical detail for one primitive 201. As noted previously, there are 50 branches (B1, B2 etc. through B50) of resistors 104 in series, each branch having six resistors 104 placed across the fluid delivery slot 232. The electrical connection to the controller 24 is shown schematically. This electrical layout decreases the current by increasing resistance; each resistor (heat transducer) 104 has a value of about 60 ohm, so the equivalent resistance of each primitive 201 is about 7.2 ohm.

The nozzles are laid out in the drop ejection device 100 in series and parallel arrangement—the illustrated embodiment shows each primary having 50 nozzles in series with six parallel groups to define the 300 nozzle primary. The electrical wiring arrangement is configured to provide a resistance of at least about 100 ohms per series connection, and more preferably about 300 ohms per series connection.

In operation, controller 24 is configured to fire or energize a matrix of heat transducers 104 in specific firing groups. Specifically, controller 24 is configured to fire any of the 30 nozzle firing groups 201-230 either individually, or together in any combination, although the preferred energizing architecture is firing two primaries in a ganged group. The number of resistors 104 that are fired depends upon the numbers of orifices formed in drop generator 100 and the arrangement of the orifices on the die. With reference to the illustrated drop ejection device 100, controller 24 is operable to energize at once a minimum of 300 heat transducers associated with the 300 orifices in any one firing group, or the heat transducers associated with all of the firing groups and any combination between those two boundaries. Accordingly, 300 nozzles are being fired at a minimum at any one time. It will be appreciated that a drop generator having fewer heat transducers may require that fewer nozzles are simultaneously energized.

Figure 14:
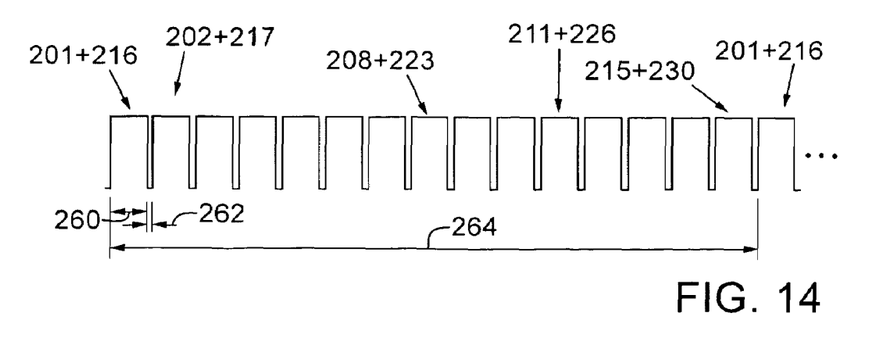
FIG. 14 is a primitive or nozzle firing group timing diagram illustrating a preferred firing order.

With reference to FIG. 14, a nozzle firing timing diagram is shown for a drop generator 100 firing at a frequency of 200 KHz. As noted, each of the two COMs 250, 252 has control over 15 primitives. Controller 24 is preferably programmed to energize (i.e., to fire) only two primitives at the same time, and always such that the two primitives that are being fired are spaced apart on the drop generator head. Thus, as illustrated in FIG. 14, controller 24 fires primitives 201 and 216 simultaneously. The firing pulse is about 300 ns, as shown by arrow 260. Referring back to FIGS. 9 and 10, it may be seen that the two primitives 201 and 216 that fire at the same time are physically and spatially separated on the drop ejection device 100. This minimizes the amount of drop merging that occurs between drops ejected from nozzles in primitive 201, and drops simultaneously ejected from nozzles in primitive 216. Stated in another way, because simultaneously fired nozzles are physically separated on the drop ejection device, individual drops ejected from different nozzles are less likely to collide with other drops and thereby coalesce into larger drops. This improves the efficiency of the drop generator head.

Continuing with FIG. 14, after primitives 201 and 216 have been fired during the pulse 260 (300 ns), there is a momentary delay, represented by arrow 262, during which controller 24 is not energizing any primitives. Delay 262 is about 33 ns. After delay 262, controller 24 then fires two different primitives, in the illustration of FIG. 4, primitives 202 and 217. Referring again to FIGS. 9 and 19, primitives 202 and 217 are physically spaced apart on the die. After a pulse of 300 ns, there is once again a delay of about 33 ns, after which two more primitives are fired—203 and 218.

This firing architecture continues until all of the primitives have been fired in paired but physically separated groups. At a firing frequency of 200 KHz, the total pulse time 264 required for each of the 15 pairs of primitives to complete one firing cycle is about 5 µs.

After one complete firing cycle is finished, controller 24 again energizes primitives 201 and 216, as shown in FIG. 14, and this firing order continues until the operator switch 30 is deactivated.

By energizing or "firing" heat transducers 104 in ganged groups such as just described, energy efficiency is maximized. Because the two primaries that are fired simultaneously are spaced apart on the drop generator 100, drop merging is minimized.

Table 1 provides selected design specification criteria for drop ejection device 100.

TABLE 1

| Design Specification Criteria | Value |
|---|---|
| Turn on energy (μJ) | 0.011-0.017[1] |
| Drop velocity (m/s) | >10 |
| Drop volume (fL) | <15 |
| Drop size (μm) | <3 μm |
| Firing Frequency (KHz) | >25, preferably about 200 |
| Nozzle Density (nozzles/mm$^2$) | >100, preferably >250 |
| Drop Generation Rate (drops per second) | >1 × 10$^9$, preferably 1.8 × 10$^9$ |
| Number of Nozzles/drop ejector device | >4,000, preferably 9000 |

Notes:
[1]The turn on energy varies depending upon the nozzle architecture as shown in FIGS. 5 through 8.

Notes:

1. The turn on energy varies depending upon the nozzle architecture as shown in FIGS. 5 through 8.

Firing drop generator 100 described herein having 9000 nozzles at a frequency of 200 KHz results in the generation of 1.8 billion droplets per second. For purposes herein, flux or total particle flux refers to the number of droplets ejected per unit time from the drop ejection device 100. A greater number of nozzles firing simultaneously increases the flux. Suitable flux is attained with a drop generator having at least about 4000 nozzles firing at a frequency of at least about 100 KHz. A drop generator operating within these constraints provides for accurate dosage control and delivery of medication in a handheld MDI 10.

When the TOE is in the range specified in Table 1, a standard power supply 28 such as batteries configured for use in an MDI 10 provides sufficient battery life.

The fluid characteristics of medication delivered to drop generator 100 can have significant impact on the performance of the MDI 10 and the droplets delivered through it. For example, an exemplary range of fluid medications for delivery through nozzle generator 100 have surface tensions in a range of about 20 to 70 dynes/cm$^2$. In a drop ejection device 100 of the type disclosed herein, an acceptable gauge pressure operating range for effective drop generator 101 operation preferably extends below about −10 inches of water (for medications having surface tension in the range noted above, 20 to 70 dynes/cm$^2$) measured proximate to the drop generator 101. Tests have shown that with medication having a surface tension at or near the low end of this range, 20 dynes/cm$^2$, and with a nozzle orifice size of about 3.0 μm, a gauge pressure operating range of about −13 inches of water is achieved. As the nozzle orifice size decreases, the effective gauge pressure operating range increases. With medication having a surface tension at or near the upper end of the range noted, 70 dynes/cm$^2$, and with a nozzle orifice size of about 3.0 μm, a gauge pressure operating range of about −45 inches of water is achieved.

When drop generator 100 thus is fabricated with orifice architectures of the type described above, the drop generators 101 are operable with a gauge pressure below about −10 inches of water, even with medications having a surface tension as low as 20 dynes/cm$^2$. Having a broad acceptable gauge pressure range has significant beneficial effects on the reliability of the MDI 10. For example, the drop generator is very shock resistant and the occurrence of shock depriming of the drop generators and bubble ingestion is substantially reduced. The drop generators are also operable under a wide range of medication fluid characteristics such as surface tension, and delivery pressures.

Having here described illustrated embodiments of the invention, it is anticipated that other modifications may be made thereto within the scope of the invention by those of ordinary skill in the art. It will thus be appreciated and understood that the spirit and scope of the invention is not limited to those embodiments, but extend to the various modifications and equivalents as defined in the appended claims.

The invention claimed is:

1. A medication delivery apparatus, comprising:

a thermal-type drop ejection device including at least 4000 drop generators, each drop generator including a nozzle, each nozzle being configured to fire at a frequency of at least 100 KHz, each drop ejected from each nozzle being from about 0.1 μm to about 15 μm in diameter;

a fluid delivery system configured to deliver fluid to the drop generators;

circuitry electrically coupled to the drop generators and configured to deliver drop ejection pulses to the drop generators; and a controller capable of delivering drop ejection pulses simultaneously to separate drop generators that are spaced apart on the drop ejection device.

2. The medication delivery apparatus according to claim 1 wherein the drop generators are arranged in plural groups, each group comprising plural drop generators individually electrically connected to a COM terminal and each COM terminal electrically connected to the controller.

3. The medication delivery apparatus according to claim 2 wherein the controller is configured for delivering drop ejection pulses to all of the drop generators in a group.

4. The medication delivery apparatus according to claim 3 wherein the controller is configured for delivering drop ejection pulses simultaneously to all of the drop generators in plural groups.

5. The medication delivery apparatus according to claim 4 wherein each group in the plural groups to which drop ejection pulses are delivered is physically separated from each other group to which drop ejection pulses are simultaneously delivered.

6. The medication delivery apparatus according to claim 1 wherein each drop ejection pulse has a duration of about 300 ns.

7. The medication delivery apparatus according to claim 6 wherein after a drop ejection pulse is delivered the controller stops delivery of drop ejection pulses for an interval.

8. The medication delivery apparatus according to claim 7 wherein the interval has a duration of about 33 ns.

9. The medication delivery apparatus according to claim 1 wherein drop ejection pulse is defined by a turn on energy of between about 0.011 to about 0.017 μJ.

10. The medication delivery apparatus according to claim 1 wherein each drop generator includes an orifice overlaying a heat transducer and wherein the heat transducer is electrically coupled to the controller.

11. The medication delivery apparatus according to claim 10 in which the controller is capable of energizing at least about 300 heat transducers simultaneously.

12. A method of energizing thermal-type drop generators in a metered dose inhaler having an ejector device, comprising the steps of:

(a) supplying fluid medication to drop generators arranged in groups on the ejector device, each group comprising plural drop generators and each group spatially separated from each other group; and (b) simultaneously applying electrical firing pulses to plural groups to simultaneously energize plural drop generators in plural groups, wherein there are at least 4000 drop generators, each drop generator including a nozzle, each nozzle firing at a frequency of at least 100 KHz, each drop ejected from each nozzle being from at least 0.1 µm to about 15 µm in diameter.

13. The method according to claim 12 wherein the two groups are simultaneously energized.

14. The method according to claim 13 wherein the two groups are energized for an activation period of about 300 ns.

15. The method according to claim 14 wherein the activation period is followed by a deactivation period of about 33 ns during which no drop generators are energized.

16. The method according to claim 15 wherein the deactivation period is followed by a second activation period having a duration of about 300 ns.

17. A handheld inhaler, comprising:
a drop ejection device including a multiplicity of thermal-type fluid drop generators arranged in a plurality of groups, each group including a multiplicity of drop generators; and control circuitry coupled to each drop generator and configured to simultaneously provide a firing pulse to all of the drop generators in at least two of the groups;

wherein there are at least 4000 drop generators, each drop generator including a nozzle, each nozzle being configured to fire at a frequency of at least 100 KHz, each drop ejected from each nozzle being from about 0.1 μm to about 15 μm in diameter.

18. The handheld inhaler according to claim 17 wherein the at least two groups to which a firing pulse is provided are physically separated from one another.

19. The handheld inhaler according to claim 17 wherein each drop generator further comprises a resistor having a resistance of about 60 ohm.

20. The handheld inhaler according to claim 18 including at least thirty groups, each group having at least about 300 drop generators, and wherein the control circuitry provides simultaneously a firing pulse to all of the drop generators in two groups.

21. The handheld inhaler according to claim 20 wherein the firing pulse has a duration of about 300 ns.

22. The handheld inhaler according to claim 21 wherein all of the drop generators are fired sequentially in simultaneously fired pairs of groups, each group in the simultaneously fired pair being spatially separated from one another.

23. The handheld inhaler according to claim 22 wherein all of the drop generators are fired in a firing cycle having a duration of about 5 μs.

24. A method of minimizing merger of drops ejected from a metered dose inhaler, comprising the steps of:

(a) arranging thermal-type drop generators on a drop ejection device in plural groups, each group comprising plural drop generators and each group spatially separated on the drop ejection device from adjacent groups;

(b) simultaneously ejecting drops from the drop generators in at least two groups by energizing all of the drop generators in the at least two groups;

wherein there are at least 4000 drop generators, each drop generator including a nozzle, each nozzle firing at a frequency of at least 100 KHz, each drop ejected from each nozzle being from about 0.1 μm to about 15 μm in diameter.

25. The method according to claim 24 wherein step (b) further comprises the step of simultaneously energizing all of the drop generators in the at least two groups with a first energized pulse having a duration of about 300 ns.

26. The method according to claim 25 including the step of a first delay after the first energized pulse during which no drop generators are energized, and wherein the first delay has a duration of about 33 ns.

27. The method according to claim 26 wherein all groups are sequentially energized in pairs with a delay after each pair in a group is energized, and wherein said drop generator generates drops at a rate of about $1\times10^9$ per second.

* * * * *

UNITED STATES PATENT AND TRADEMARK OFFICE
CERTIFICATE OF CORRECTION

| | |
|---|---|
| PATENT NO. | : 7,469,696 B2 |
| APPLICATION NO. | : 11/044660 |
| DATED | : December 30, 2008 |
| INVENTOR(S) | : Yang et al. |

Page 1 of 1

It is certified that error appears in the above-identified patent and that said Letters Patent is hereby corrected as shown below:

In column 11, line 8, delete "at least" and insert -- about --, therefor.

Signed and Sealed this

Seventeenth Day of November, 2009

David J. Kappos
*Director of the United States Patent and Trademark Office*